United States Patent [19]

Murakoshi et al.

[11] Patent Number: 4,473,841
[45] Date of Patent: Sep. 25, 1984

[54] VIDEO SIGNAL TRANSMISSION SYSTEM FOR ENDOSCOPE USING SOLID STATE IMAGE SENSOR

[75] Inventors: Makoto Murakoshi, Asaka; Morihiko Yoshida, Omiya, both of Japan

[73] Assignees: Fuji Photo Film Co., Ltd., Kanagawa, Japan; Fuji Photo Optical Co., Ltd., Saitama, both of Japan

[21] Appl. No.: 424,768

[22] Filed: Sep. 27, 1982

[30] Foreign Application Priority Data

Oct. 20, 1981 [JP]  Japan .................................. 56-167570

[51] Int. Cl.³ .......................... A61B 1/04; H04B 9/00
[52] U.S. Cl. .......................................... 358/98; 128/6; 358/901; 455/612
[58] Field of Search .................. 358/98; 128/3-8; 358/901, 86; 455/610, 612

[56] References Cited

U.S. PATENT DOCUMENTS

| Re. 31,289 | 6/1983 | Moore | 358/98 |
|---|---|---|---|
| 3,324,326 | 6/1967 | Sheldon | 358/98 |
| 3,328,594 | 6/1967 | Sheldon | 358/98 |
| 4,074,306 | 2/1978 | Kakinuma | 128/6 |
| 4,149,186 | 4/1979 | Chung | 358/86 |
| 4,183,054 | 1/1980 | Patisaul | 358/86 |

*Primary Examiner*—Howard W. Britton
*Attorney, Agent, or Firm*—Birch, Stewart, Kolasch & Birch

[57] ABSTRACT

A video signal transmission system for an endoscope converts an electrical video signal produced by a solid state image sensor into an optical signal and transmits the optical signal to a control section through a fiber optic cable or like light carrying medium. Because the fiber optic cable used for the present invention transmits light indicative of a time serial signal from the solid state imaging sensor, it will be clear that the cable may be constituted by a single length of optical fiber and, in this respect, substantially differs from usual light carrying fiber bundles which are installed in general endoscopes as image guides for transmitting light images simply as light.

7 Claims, 2 Drawing Figures

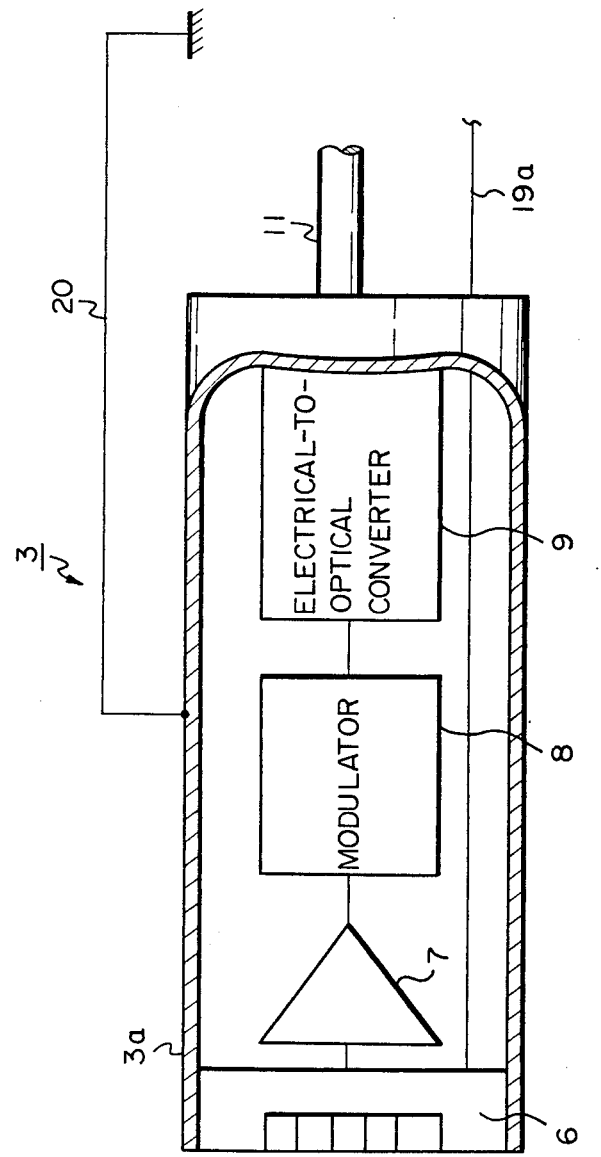

VIDEO SIGNAL TRANSMISSION SYSTEM FOR ENDOSCOPE USING SOLID STATE IMAGE SENSOR

BACKGROUND OF THE INVENTION

1. Field of the Invention

The present invention relates to a video signal transmission system for an endoscope of the type having in its imaging system a solid state image sensor, such as a charge coupled device (CCD), a bucket brigade device (BBD), as referred to as a charge transfer device.

2. Description of the Prior Art

As well known in the art, an endoscope includes a viewing head which carries therein an imaging system, an illumination system, a forceps, a treating instrument, etc. A control section operates such systems and instruments of the viewing head while allowing image information picked up to be observed and recorded. The head and control sections are connected together by a flexible connecting section. A treating instrument of the head section often may take the form of a high frequency knife or scalpel. Where the endoscope employs a solid state image sensor in the imaging system in combination with the high frequency knife, the power supply line to the knife and the signal line from the imaging system are unavoidably arranged parallel to each other within the connecting section. Then, the endoscope suffers from a problem that noise is electromagnetically induced in an output signal of the imaging system by the high frequency current flowing through the power supply line to the knife, resulting in disturbance to the image which is monitored at the control section.

The disturbance to the image tends to appear itself as stripes or dots in a picture produced on a display which are objectionable for delicate operations in narrow cavities or openings and, in the worst cases, cause the operator to mislocate the surgical knife within such cavities.

SUMMARY OF THE INVENTION

In an endoscope of the type which uses a solid state image sensor for picking up an image inside a cavity of a living body, a video signal transmission system embodying the present invention includes an electrical-to-optical signal conversion means for converting a video signal generated by the solid state image sensor into an optical signal. A light transmission medium is connected with the electrical-to-optical signal conversion means to transmit the optical signal therethrough. An optical-to-electrical signal conversion means converts the optical signal propagated through the light transmission medium into an electric signal to display the image picked up.

In accordance with the present invention, a video signal transmission system for an endoscope transduces a video signal generated by a solid state image sensor into an optical signal and transmits the optical signal to a control section through a fiber optic cable or like light carrying medium. Because the fiber optic cable used for the present invention transmits light representative of a time serial electric signal produced from the solid state image sensor, it will be clear that the cable may be constituted by a single optical fiber and, in this respect, substantially differs from usual light carrying bundles which are installed in general endoscopes as image guides for transmitting light images simply as light.

It is an object of the present invention to provide a video signal transmission system for a endoscope of the type described which eliminates the shortcoming discussed above and prevents the drive current to a high frequency knife from affecting image information of a viewing region.

It is another object of the present invention to provide a generally improved video signal transmission system for an endoscope of the type described.

BRIEF DESCRIPTION OF THE DRAWINGS

The objects and features of this invention will become more apparent from a consideration of the following detailed description and the drawing in which:

FIG. 2 schematically shows in partly cutaway view the construction of an imaging arrangement included in the endoscope indicated in FIG. 1.

DESCRIPTION OF THE PREFERRED EMBODIMENT

Figure 1:
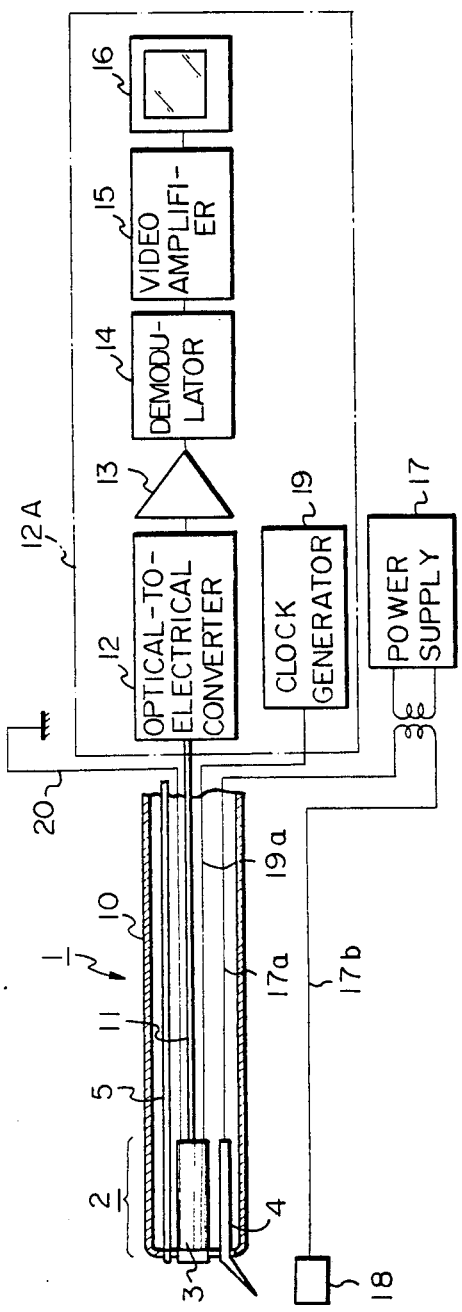
FIG. 1 shows, schematically in cross section and partially in a block diagram, an endoscope with a solid state image sensor which incorporates a video signal transmission system of the present invention.

Referring to FIG. 1 of the drawing, an endoscope incorporating the video signal transmission system of the present invention is shown and generally designated by the reference numeral 1. The endoscope 1 comprises a head section or viewing head 2 which includes an imaging portion 3, an electrode portion 4 functioning as a high frequency knife or scalpel, and a light guide 5 for transmitting light therethrough to illuminate a desired region inside a cavity of a living body (not shown). As seen in FIG. 2, the imaging portion 3 comprises a self-scanning solid state image sensor such as a charge coupled device (CCD) 6, an amplifier 7, a modulator 8 and an electrical-to-optical signal converter 9 as typified by a light emitting diode or a semi-conductor laser. The imaging portion 3 is encircled by a cylindrical metal tube 3a which is open at one end thereof. The metal tube 3a is connected to ground, a reference voltage, by a lead 20 for electromagnetic shielding. A fiber optic cable 11 is disposed in a connecting section 10 shown in FIG. 1 and may comprise at least a single length of optical fiber. The electrical-to-optical signal converter 9 is connected to the light inlet end of the fiber optic cable 11. The light outlet end of the cable 11 connects to an optical-to-electrical signal converter 12 which is included in a control section 12A for manipulating the endoscope. The modulator 8 modulates a carrier with an image signal produced from image sensor 6 in a known manner such as for amplitude modulation, frequency modulation, phase modulation or pulse code modulation. In the case of baseband transmission as may be desired, the modulator 8 will be omitted.

With the above construction, the solid state CCD imager 6, when clocked by a clock generator 19, produces a video signal in a raster scanning fashion, which signal represents the scene of the region imaged thereby. The video signal is amplified by the amplifier 7 and then modulates a carrier in the modulator 8. The output of the modulator 8 is converted by the electrical-to-optical signal converter 9 into a time serial optical signal modulated in brightness. The optical signal propagates through the fiber optic cable 11 to reach the phototransistor or like optical-to-electrical signal converter 12, which is connected with the light outlet end of the cable 11. The electric output of the converter 12 is coupled as a video signal to a display 16 through a signal processing system which includes a preamplifier 13, a demodulator 14, and a video amplifier 15. The image display 16 may be a cathode-ray tube (CRT), for example. It will be seen that the demodulator 14 will also be omitted in the case of baseband transmission.

A power source 17 supplies the electrode section or surgical knife 4 with a high frequency current through a power source line 17a which extends through the connecting section 10 along the length of the latter and substantially in parallel with the fiber optic cable 11. The other power source line 17b from the power source 17 terminates at an electrode plate 18 which is located outside the endoscope and fitted to the living body.

When the output signal of the solid state imager is transmitted in the form of an optical signal through the fiber optic cable 11 in the manner described above, the supply of high frequency current to the knife during operation is prevented from electromagnetically affecting the optical video signal which propagates through the fiber optic cable 11. This eliminates disturbance to the image on the display 16. The reference numeral 19 in FIG. 1 denotes a clock generator adapted to drive or clock the CCD imager 6. The clock pulses from the clock generator 19 are fed to the CCD imager 6 by a lead 19a.

In summary, it will be seen that the present invention permits a video signal from a solid state image sensor to propagate through a transmission system without any noise due to external high frequency signals or the like, because the transmission of the video signal relies on a fiber optic cable. It will also be seen that the image monitored at a control section is prevented from being disturbed during the use of a high frequency knife by a metal enclosure which electromagnetically shields the image sensor and its associated electronic circuitry.

While the present invention has been described in terms of a specific illustrative embodiment, it is to be understood to be susceptible of modification by those skilled in the art within the spirit and scope of the appended claims.

What is claimed is:

1. A video signal transmission for an endoscope of the type which uses a solid state image sensor for picking up an image inside a cavity of a living body, comprising:
   electrical-to-optical signal conversion means for converting a video signal produced by the solid state image sensor into an optical signal;
   light transmission means connected with said electrical-to-optical signal conversion means for transmitting the optical signal thereover; and
   optical-to-electrical signal conversion means for converting the optical signal propagated through the light transmission means into an electrical signal to display the image picked up.

2. A video signal transmission system in accordance with claim 1, wherein the solid state image sensor and electrical-to-optical signal conversion means are electromagnetically shielded.

3. A video signal transmission system for an endoscope of the type including a head portion to be inserted into a cavity of a living body, a control unit for manipulating the endoscope, and a connecting portion for connecting the head portion with the control unit, said head portion including a solid state image sensor for picking up an image inside the cavity to produce an electrical image signal, comprising:
   electrical-to-optical signal conversion means included in the head portion for converting the electrical video signal into an optical signal associated therewith;
   a light transmission medium extending within the connecting portion for transmitting the optical signal from said electrical-to-optical signal conversion means to the control unit; and
   optical-to-electrical conversion means included in the control unit to receive the optical signal transmitted over the light transmission medium for converting the optical signal into an electrical signal associated therewith to display the picked-up image.

4. A video signal transmission system in accordance with claim 3, further comprising modulator means included in the head portion for modulating a carrier with the electrical video signal to supply said electrical-to-optical conversion means with a modulated signal, and demodulator means included in the control unit for demodulating the electrical signal produced from said optical-to-electrical signal conversion means into a baseband signal representative of the image picked up.

5. A video signal transmission system in accordance with claim 4, further comprising shielding means for substantially surrounding and electromagnetically shielding said image sensor, electrical-to-optical signal conversion means and modulator means.

6. A video signal transmission system for an endoscope of the type including a head portion to be inserted into a cavity of a living body, a control unit for manipulating the endoscope, and a connecting portion for connecting the head portion with the control unit, said head portion including a solid state image sensor for picking up an image inside the cavity to produce an electrical video signal, comprising:
   electrical-to-optical signal conversion means included in the head portion for converting the electrical video signal into an optical signal associated therewith;
   optical fiber means connected to said electrical-to-optical signal conversion means and extending within the connecting portion for transmitting the optical signal from said electrical-to-optical signal conversion means to the control unit;
   optical-to-electrical conversion means included in the control unit and connected to receive the optical signal transmitted over the optical fiber means for converting the optical signal into an electrical signal associated therewith to display the picked-up image; and
   a metal enclosure included in the head portion and connected to a reference voltage for substantially surounding said image sensor and electrical-to-optical signal conversion means so as to electromagnetically shielding said image sensor and electrical-to-optical signal conversion means.

7. A video signal transmission system in accordance with claim 6, further comprising a modulator circuit included in said enclosure for modulating a carrier with the electrical video signal to supply said electrical-to-optical signal conversion means with a modulated signal, and a demodulator circuit included in the control unit for demodulating the electrical signal produced from said optical-to-electrical signal conversion means into a baseband signal representative of the image picked up.

* * * * *